United States Patent [19]
Braun et al.

[11] Patent Number: 5,894,075
[45] Date of Patent: Apr. 13, 1999

[54] CATALYTIC MIXTURES COMPOSED OF TITANIUM AND TIN AND USES THEREOF

[75] Inventors: Max Braun, Wedemark; Werner Rudolph, Hannover; Stefan Palsherm, Barsinghausen, all of Germany

[73] Assignee: Solvay Fluor und Derivate GmbH, Hannover, Germany

[21] Appl. No.: 08/773,495

[22] Filed: Dec. 23, 1996

[30] Foreign Application Priority Data

Dec. 28, 1995 [DE] Germany ............... 195 48 999

[51] Int. Cl.⁶ .................................. C07C 17/08
[52] U.S. Cl. ................................................ 570/168
[58] Field of Search ................................... 570/168

[56] References Cited

U.S. PATENT DOCUMENTS

| | | |
|---|---|---|
| 5,008,474 | 4/1991 | Walraevens et al. |
| 5,159,126 | 10/1992 | Walraevens et al. |
| 5,347,059 | 9/1994 | Pennetreau et al. |
| 5,382,721 | 1/1995 | Pennetreau et al. |
| 5,395,997 | 3/1995 | Van Der Puy |

FOREIGN PATENT DOCUMENTS

| | | |
|---|---|---|
| 391102 | 10/1990 | European Pat. Off. |
| 574077 | 12/1993 | European Pat. Off. |
| 675096 | 10/1995 | European Pat. Off. |
| 27 39 478 | 3/1978 | Germany. |
| 627773 | 8/1949 | United Kingdom. |

OTHER PUBLICATIONS

Fiering, "Chemistry in Hydrogen Fluoride v. Catalysts for Reaction of HF with Halogenated Olefins", *Journal of Fluorine Chemistry*, 14 (1979), pp. 7–18.

*Primary Examiner*—Alan Siegel
*Attorney, Agent, or Firm*—Evenson, McKeown, Edwards & Lenahan, P.L.L.C.

[57] ABSTRACT

The addition of hydrogen fluoride to unsaturated C—C groups and the chlorine-fluorine exchange on perhalogenated carbon atoms can be advantageously catalyzed by a catalyst mixture which comprises at least partially fluorinated titanium halide in combination with tin (IV) halide.

13 Claims, No Drawings

CATALYTIC MIXTURES COMPOSED OF TITANIUM AND TIN AND USES THEREOF

BACKGROUND OF THE INVENTION

The present invention relates to catalytic mixtures on the basis of at least partially fluorinated titanium tetrachloride and tin tetrachloride and their use for the production of fluorinated organic compounds.

A large number of catalysts are already known which are suitable for the addition of hydrogen fluoride (HF) and for chlorine-fluorine exchange by means of hydrogen fluoride.

For example, U.S. Pat. No. 5,347,059 (=EP 522,638) discloses a process for the production of 1,1-dichloro-1,3,3,3-tetrafluoropropane from the corresponding hexachloropropane compound. Metals of the groups IIIa, IVa and b, Va and b and group VIb of the periodic table of the elements and their mixtures are cited as catalysts which promote the reaction. Titanium derivatives, tantalum derivatives, molybdenum derivatives, boron derivatives, tin derivatives and antimony derivatives are particularly suitable. Tin derivatives and antimony derivatives are emphasized as being particularly preferred.

U.S. Pat. No. 5,202,509 (=EP 415,814) discloses fluorination catalysts which consist of a mixture of an antimony trihalide and a titanium tetrahalide. These mixtures are suitable, for example, for the fluorination of chlorine derivatives of methane, ethane and ethylene. However, corresponding bromine or iodine derivatives can also be fluorinated.

A. E. Feiring in J. Fluorine Chem. 14 (1979), pages 7 to 18, discloses that $TiCl_4$ catalyses the addition of HF to tetrachloroethylene. A subsequent chlorine-fluorine exchange leads to the formation of difluorotrichloroethane to a small extent.

Published British Patent Application No. GB 627,773 discloses the addition of hydrogen fluoride to certain C2 and C3 compounds. The catalyst is tin tetrachloride and tin tetrafluoride. In addition to the HF addition, a chlorine-fluorine exchange is also observed.

U.S. Pat. No. 5,395,997 (=WO 95/04021) discloses the production of fluorohydrocarbons from chlorohydrocarbons, which may also be fluorine-substituted, by catalyzed chlorine-fluorine exchange with hydrogen fluoride. Preferably at least one metal halide, selected from the group of halides of tin, titanium, tantalum and antimony is used. The examples operate with antimony pentafluoride, titanium tetrachloride, tin tetrachloride, antimony pentachloride or in the absence of a catalyst.

SUMMARY OF THE INVENTION

It is an object of the present invention to provide a metal halide catalyst system with high activity.

Another object of the invention is to provide a process for use of such a catalyst system.

These and other objects are achieved in accordance with the present invention by providing a liquid-phase process for producing organic compounds containing at least one fluorine atom, comprising introducing at least one fluorine atom by metal halide catalyzed addition of HF to an unsaturated C—C group or by metal halide catalyzed chlorine-fluorine exchange of HF with at least one fully halogenated C atom in a starting material, wherein the introducing step is carried out in the presence of a metal halide catalyst comprising an at least partially fluorinated mixture of titanium chloride or titanium bromide in combination with at least partially fluorinated tin tetrachloride or tin tetrabromide in which titanium and tin are present in an atomic ratio in the range from 9:1 to 1:9.

The objects are also achieved in accordance with a further aspect of the invention by providing an at least partially fluorinated mixture of titanium tetrachloride or titanium tetrabromide in combination with tin tetrachloride or tin tetrabromide, the mixture having an atomic ratio of titanium to tin in the range of from 1:9 to 9:1, and being a reaction product of hydrogen fluoride with titanium tetrachloride or titanium tetrabromide and tin tetrachloride or tin tetrabromide in a molar ratio of HF to the sum of titanium tetrachloride or tetrabromide and tin tetrachloride or tetrabromide of at least 4:1.

DETAILED DESCRIPTION OF PREFERRED EMBODIMENTS

The invention is based on the observation that mixtures of at least partially fluorinated titanium halides in combination with tin tetrahalides have a catalyst activity which is increased relative to the catalytic activities of the individual constituents.

The process according to the invention in the liquid phase for producing organic compounds having at least one fluorine atom, in which at least one fluorine atom is introduced by addition, catalyzed by metal halide, of hydrogen fluoride to an unsaturated C—C group or by a chlorine-fluorine exchange, catalyzed by metal halide, using hydrogen fluoride on at least one fully halogenated C atom in the starting material, provides for operating in the presence of an at least partially fluorinated mixture of titanium chloride or titanium bromide in combination with at least partially fluorinated tin tetrachloride or tin tetrabromide as metal halide, with the proviso that the atomic ratio of titanium to tin is in the range of 9:1 to 1:9.

Of course, the titanium can also be used in the form of an at least partially fluorinated mixture of titanium chloride and titanium bromide, and the tin in the form of an at least partially fluorinated mixture of tin tetrachloride and tin tetrabromide. Advantageously, the starting point is titanium tetrachloride and tin tetrachloride. This embodiment will be explained in greater detail below.

It is most particularly advantageous to use a catalyst mixture which is obtained by reacting titanium tetrachloride and tin tetrachloride with hydrogen fluoride, the molar ratio of hydrogen fluoride to the total of titanium tetrachloride and tin tetrachloride being at least 4:1, preferably at least 8:1. Those catalyst mixtures which are obtained if titanium tetrachloride and tin tetrachloride are reacted at a temperature of at least 145° C. over a period of at least 150 minutes with at least an 18 times molar quantity of hydrogen fluoride relative to the chlorine atoms of the tin tetrachloride/titanium tetrachloride mixture are particularly suitable.

The catalyst mixture of at least partially fluorinated tin tetrahalide and titanium tetrahalide can be used for those production processes in which a hydrogen fluoride addition and/or a chlorine-fluorine exchange is carried out using hydrogen fluoride in the presence of a titanium tetrahalide catalyst or tin tetrahalide catalyst. It therefore falls within the scope of the present invention that in known fluorination processes which are catalyzed by means of tin halide or titanium halide this catalyst is replaced by the above mixtures of at least partially fluorinated tin halide and titanium halide.

The liquid-phase process according to the invention is particularly well suited for the production of C2–C8 alkanes which have at least one fluorine atom and also for the production of C2–C8 alkanes which have at least one fluorine atom and additional halogen substituents. In order to produce them, one can start with corresponding C2–C8 alkenes and add hydrogen fluoride in the presence of the catalyst mixtures according to the invention.

The process is also highly suitable for converting C2–C8 alkanes which have one or more fully halogenated carbon atoms, in particular C2–C8 alkanes having one or more $CCl_3$, $CCl_2F$ or $CClF_2$ groups, with chlorine-fluorine exchange using HF, into compounds which have at least one fluorine atom more than the starting compounds.

The process according to the invention is outstandingly suited for the production of alkanes which have at least one fluorine atom more than the alkene used, in which case alkenes of the formula $CX^1X^2=CX^3X^4$ are used, wherein $X^1$ represents chlorine, fluorine, $CCl_3$, $CCl_2F$, $CClF_2$ or $CF_3$, and $X^2$, $X^3$ and $X^4$ independently of each other represent hydrogen, chlorine or fluorine, and corresponding alkanes are produced by HF addition and optionally additional chlorine-fluorine exchange.

The process is very outstandingly suitable for chlorine-fluorine exchange in alkanes of the formula $CX^5X^6X^7CX^8X^9X^{10}$, wherein $X^5$ represents $CCl_3$, $CCl_2F$, $CClF_2$ or chlorine, $X^6$ and $X^7$ represent chlorine or fluorine, or, if $X^5$ is not chlorine, $X^6$ and $X^7$ independently of each other each represent chlorine, fluorine or hydrogen, and $X^8$, $X^9$ and $X^{10}$ independently of each other represent hydrogen, chlorine or fluorine.

For example, perchloroethylene can be reacted to form fluorotetrachloroethane, difluorotrichloroethane or trifluorodichloroethane. For instance, it is also possible to react 1-fluoro-1,1,2,2-tetrachloroethane to 1,1-difluoro-1,2,2-trichloroethane and 1,1,1-trifluoro-2,2-dichloroethane according to the process of the invention.

The atomic ratio of titanium to tin is preferably in the range of 2:1 to 1:2. In this case, it has been demonstrated that such a mixture with a molar ratio of titanium to tin in the range of 2:1 to 1:2 not only catalyses the HF addition to double or triple bonds well, but chlorine-fluorine exchange on $CCl_3$, $CCl_2F$ or $CF_2Cl$ groups with formation of $CF_3$ groups becomes possible.

The molar ratio of the educt to the total of the catalyst mixture is between 1:0.1 and 1:5.

The temperature during the reaction is advantageously in the range of 30 to 250° C. The pressure is adjusted such that one operates in the liquid phase. If one operates in an autoclave, an autogenous pressure builds up due to the presence of hydrogen fluoride and possibly released HCl. The autogenous pressure which develops is of course also dependent on the temperature of the reaction mixture. Expediently, the pressure can be adjusted such that it lies within a range of 2 to 80 bar (absolute).

A further subject of the present invention is an at least partially fluorinated mixture of titanium tetrachloride and tin tetrachloride having an atomic ratio of titanium to tin in the range of 9:1 to 1:9, in particular 2:1 to 1:2, obtainable by reacting titanium tetrachloride and tin tetrachloride with hydrogen fluoride, the molar ratio of HF to the total of titanium tetrachloride and tin tetrachloride being at least 4:1, preferably at least 8:1. Such a mixture can be used as a catalyst for hydrogen fluoride addition to C—C double bonds and C—C triple bonds, and as a catalyst for the chlorine-fluorine exchange using hydrogen fluoride as fluorine source in trichloromethyl, fluorodichloromethyl and difluorochloromethyl groups, in particular with regard to the production of compounds with the $CF_3$ group.

The advantages of the process according to the invention is the high conversion and the high yield and also the high selectivity, and, in preferred embodiments, also the possibility of producing $CF_3$ groups with Ti/Sn catalysts.

The following examples of the invention and comparison examples are intended to illustrate the invention in further detail without restricting its scope.

EXAMPLES

Example 1

General procedure for preliminary fluorination of the catalyst or catalyst mixtures.

A twenty-fold molar amount of hydrogen fluoride was added to the stated quantities of catalyst in a 250 ml autoclave manufactured by Roth in an aluminum inliner and was pre-fluorinated for 3 hours at the listed reaction temperature. The excess HF and the resulting HCl were discharged into a scrubber after the preliminary fluorination had ended and the autoclave had cooled down. When using pure $TiCl_4$ as catalyst, after the preliminary fluorination $TiCl_{0.1}F_{3.9}$ was obtained, and pure $SnCl_4$ was fluorinated to form $SnCl_{2.7}F_{1.3}$, i.e. the preliminary fluorination procedure had only partially replaced the chlorine atoms by fluorine atoms.

The preliminary fluorination in an autoclave without aluminum inliner yielded comparable results, as did the syntheses of halogenated hydrocarbons.

Example 2

Hydrofluorination of perchloroethylene with pure $TiCl_4$ as catalyst (comparison example).

23.4 g (0.123 mole) $TiCl_4$ were used for the preliminary fluorination. After the preliminary fluorination of the catalyst mixture, 78.4 g (0.473 mole) tetrachloroethylene (PCE) and then 100.0 g (4.998 mole) HF were placed in the autoclave and the autoclave was heated to an internal temperature of 150° C. in an oil bath. A sample for analysis (given in percent gas chromatography area) taken from the gas phase via a washing bottle after a reaction time of three hours consisted only of 21.1% $CF_2Cl$—$CHCl_2$ (122) and 78.9% educt perchloroethylene (PCE). The temperature was maintained at 150° C. overnight and the contents of the autoclave after cooling were transferred quantitatively into ice water. The organic phase contained as reaction products 19.5% 122 and 80.5% 121. The conversion of PCE was 12.2%.

Example 3

43.2 g (0.228 mole) $TiCl_4$ were used for the preliminary fluorination as a mixture with 6.6 g (0.025 mole) $SnCl_4$. After the preliminary fluorination of the catalyst mixture, 77.9 g (0.470 mole) tetrachloroethylene (PCE) and then 97.8 g (4.888 mole) HF were poured into the autoclave and the autoclave was heated to an internal temperature of 150° C. in an oil bath. A sample for analysis (given in percent gas chromatography area) taken from the gas phase via a washing bottle after a reaction time of three hours consisted of 0.086% $CF_3CHCl_2$ (123), 18.894% $CF_2Cl$—$CHCl_2$ (122), 25.382% $CFCl_2$—$CCl_2H$ (121) and 55.638% educt perchloroethylene (PCE). The temperature was kept at 150° C. overnight and the contents of the autoclave after cooling were transferred quantitatively into ice water. The organic phase contained as reaction products 0.6% 123, 67.46% 122 and 32.0% 121. The conversion of PCE was 67.1%.

Example 4

Hydrofluorination of perchloroethylene (PCE) with molar 1:1 mixture of $TiCl_4$ and $SnCl_4$.

11.5 g (0.061 mole) $TiCl_4$ were used for the preliminary fluorination as a mixture with 16.0 g (0.061 mole) $SnCl_4$. After the preliminary fluorination of the catalyst mixture, 50.5 g (0.305 mole) tetrachloroethylene (PCE) and then 96.2 g (4.808 mole) HF were poured into the autoclave and the autoclave was heated to an internal temperature of 150°C. in an oil bath. A sample for analysis (given in percent gas chromatography area) taken from the gas phase via a washing bottle after a reaction time of three hours consisted of 2.09% $CF_3H$ (23), 0.37% 22 ($CF_2HCl$), 7.6% $CF_3CHCl_2$ (123), 80.52% $CF_2Cl$—$CHCl_2$ (122), 2.28% $CFCl_2$—$CCl_2H$ (121) and 7.14% educt perchloroethylene (PCE). The temperature was kept at 150° C. overnight and the contents of the autoclave after cooling were transferred quantitatively into ice water. The organic phase contained as reaction products 4.97% 123, 90.67% 122 and 4.36% 121. The conversion of PCE was 86.9%.

Example 5

Hydrofluorination of perchloroethylene with molar 1:9 $TiCl_4/SnCl_4$ mixture as catalyst.

4.7 g (0.025 mole) $TiCl_4$ were used for the preliminary fluorination as a mixture with 58.2 g (0.223 mole) $SnCl_4$. After the preliminary fluorination of the catalyst mixture, 77.9 g (0.470 mole) tetrachloroethylene (PCE) and then 96.3 g (4.813 mole) HF were poured into the autoclave and the autoclave was heated to an internal temperature of 150° C. in an oil bath. A sample for analysis (given in percent gas chromatography area) taken from the gas phase via a washing bottle after a reaction time of three hours consisted of 0.031% $CF_3CHCl_2$ (123), 5.32% $CF_2Cl$—$CHCl_2$ (122), 6.07% $CFCl_2$—$CCl_2H$ (121) and 88.58% educt perchloroethylene (PCE). The temperature was kept at 150° C. overnight and the contents of the autoclave after cooling were transferred quantitatively into ice water. The organic phase contained as reaction products 0.3% 123, 57.4% 122 and 42.3% 121. The conversion of PCE was 19.3%.

Example 6

Hydrofluorination of perchloroethylene with pure $SnCl_4$ as catalyst.

33.5 g (0.129 mole) $SnCl_4$ were used for the preliminary fluorination. After the preliminary fluorination of the catalyst mixture, 76.6 g (0.462 mole) tetrachloroethylene (PCE) and then 99.4 g (4.968 mole) HF were poured into the autoclave and the autoclave was heated to an internal temperature of 150° C. in an oil bath. A sample for analysis (given in percent gas chromatography area) taken from the gas phase via a washing bottle after a reaction time of three hours contained 0.066% $CF_3CHCl_2$ (123), 11.743% $CF_2Cl$—$CHCl_2$ (122), 6.946% $CFCl_2$—$CCl_2H$ (121) and 81.16% educt perchloroethylene (PCE). The temperature was kept at 150° C. overnight and the contents of the autoclave after cooling were transferred quantitatively into ice water. The organic phase contained as reaction products 0.45% 123, 70.5% 122 and 29.05% 121. The conversion of PCE was 20.0%.

Example 7

Production of 1,1,1-trifluoro-2,2-dichloroethane from 1,1-difluoro-1,2,2-trichloroethane with 1:1 molar mixture of $TiCl_4$ and $SnCl_4$ as catalyst. 22.6 g (0.119 mole) $TiCl_4$ were used for the preliminary fluorination as a mixture with 32.0 g (0.123 mole) $SnCl_4$. After the preliminary fluorination of the catalyst mixture, 101 g (0.596 mole) $CF_2Cl$—$CHCl_2$ (122) and then 49.9 g (2.495 mole) HF were poured into the autoclave and the autoclave was heated to an internal temperature of 140° C. in an oil bath. A sample for analysis (given in percent gas chromatography area) taken from the gas phase via a washing bottle after a reaction time of three hours contained 21% $CF_3CHCl_2$ (123) and 79% the educt $CF_2Cl$—$CHCl_2$ (122). The temperature was kept at 140° C. overnight and the contents of the autoclave after cooling were transferred quantitatively into ice water. The organic phase contained only 123 as reaction product. The conversion of the reaction was however only 7%.

Example 8

(comparison example) Attempt to produce R123 from R122 with $SnCl_4$ as catalyst.

The procedure of Example 7 was repeated except that pure $SnCl_4$ was used as the catalyst. After working up the reaction mixture, only 123 was found as product. However, the conversion was only 0.9%.

Example 9

(comparison example) Attempt to produce R123 from R122 with $TiCl_4$ as catalyst.

The procedure of Example 8 was repeated except that pure $TiCl_4$ was used as the catalyst. After working up the reaction mixture, no product was found.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A liquid-phase process for producing organic compounds containing at least one fluorine atom, said process comprising introducing at least one fluorine atom by metal halide catalyzed addition of HF to an unsaturated C—C group or by metal halide catalyzed chlorine-fluorine exchange of HF with at least one fully halogenated C atom in a starting material, wherein the introducing step is carried out in the presence of a metal halide catalyst comprising an at least partially fluorinated mixture of titanium chloride or titanium bromide in combination with at least partially fluorinated tin tetrachloride or tin tetrabromide in which titanium and tin are present in an atomic ratio in the range from 9:1 to 1:9.

2. A process according to claim 1, wherein the metal halide catalyst is obtained by reacting HF with $TiCl_4$ and $SnCl_4$, wherein the molar ratio of HF to ($TiCl_4$+$SnCl_4$) is at least 4:1.

3. A process according to claim 2, wherein the molar ratio of HF to ($TiCl_4$+$SnCl_4$) is at least 8:1.

4. A process according to claim 1, wherein HF is added to a C2–C8 alkene to obtain a corresponding C2–C8 alkane containing at least one fluorine atom or a corresponding C2–C8 alkane containing at least one fluorine atom and at least one additional halogen substituent.

5. A process according to claim 4, wherein said alkene corresponds to the formula

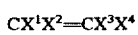

wherein $X^1$ represents chlorine, fluorine, $CCl_3$, $CCl_2F$, $CClF_2$ or $CF_3$, and $X^2$, $X^3$ and $X^4$ independently represent hydrogen, chlorine or fluorine, and wherein through the HF addition and optionally additional chlorine-fluorine exchange an alkane product is obtained containing at least one fluorine atom more than said alkene.

6. A process according to claim 5, wherein said alkene is perchloroethylene.

7. A process according to claim 1, wherein a C2–C8 alkane starting compound containing at least one $CCl_3$, $CCl_2F$ or $CClF_2$ group is subjected to chlorine-fluorine exchange with HF to obtain a corresponding alkane containing at least one fluorine atom more than the starting compound.

8. A process according to claim 7, wherein the alkane starting compound corresponds to the formula $$CX^5X^6X^7CX^8X^9X^{10}$$

wherein $X_5$ represents $CCl_3$, $CCl_2F$, $CClF_2$ or chlorine, $X^6$ and $X^7$ represent for chlorine or fluorine, and if $X^5$ is not chlorine, may also each represent hydrogen, and $X^8$, $X^9$ and $X^{10}$ independently represent hydrogen, chlorine or fluorine.

9. A process according to claim 8, wherein said alkane starting compound is 1-fluoro-1,1,2,2-tetrachloroethane or 1,1-difluoro-1,2,2-trichloroethane.

10. A process according to claim 1, wherein the atomic ratio of titanium to tin is in the range from 2:1 to 1:2.

11. A process according to claim 1, wherein said process is carried out at a pressure of from 2 to 80 bar (absolute) and a temperature of from 30 to 250° C.

12. A process according to claim 1, comprising producing a compound containing a $CF_3$ group by chlorine-fluorine exchange on a $CCl_3$, $CFCl_2$ or $CF_2Cl$ group, wherein the atomic ratio of titanium to tin is in the range from 1:2 to 2:1.

13. A method of catalyzing HF addition to C—C double bonds or C—C triple bonds or chlorine-fluorine exchange using HF in $CCl_3$, $CCl_2F$ and $CClF_2$ groups, said method comprising carrying out said HF addition or said chlorine-fluorine exchange in the presence of a catalytically effective amount of an at least partially fluorinated mixture of titanium tetrachloride or titanium tetrabromide and tin tetrachloride or tin tetrabromide having an atomic ratio of titanium to tin in the range of from 1:9 to 9:1, wherein said mixture is a product of reaction of hydrogen fluoride with titanium tetrachloride or titanium tetrabromide and tin tetrachloride or tin tetrabromide in a molar ratio of HF to the sum of titanium tetrachloride or tetrabromide and tin tetrachloride or tetrabromide of at least 4:1.

* * * * *